(12) United States Patent
Ryu et al.

(10) Patent No.: US 9,254,391 B2
(45) Date of Patent: Feb. 9, 2016

(54) SYSTEMS AND METHODS FOR DETERMINING PACING RELATED PARAMETERS

(75) Inventors: Kyungmoo Ryu, Palmdale, CA (US); Tomas Svensson, Stockholm (SE); Stuart Rosenberg, Castaic, CA (US)

(73) Assignee: Pacesetter, Inc., Sylmar, CA (US)

( * ) Notice: Subject to any disclaimer, the term of this patent is extended or adjusted under 35 U.S.C. 154(b) by 900 days.

(21) Appl. No.: 13/196,580

(22) Filed: Aug. 2, 2011

(65) Prior Publication Data

US 2013/0035737 A1   Feb. 7, 2013

(51) Int. Cl.
*A61N 1/365*   (2006.01)
*A61N 1/368*   (2006.01)
*A61N 1/37*   (2006.01)

(52) U.S. Cl.
CPC ............ *A61N 1/3682* (2013.01); *A61N 1/3684* (2013.01); *A61N 1/371* (2013.01)

(58) Field of Classification Search
CPC .... A61N 1/3684; A61N 1/3682; A61N 1/371
USPC .......................................................... 607/25
See application file for complete search history.

(56) References Cited

U.S. PATENT DOCUMENTS

| 7,546,161 B1 | 6/2009 | Bjorling et al. |
| 2006/0155338 A1 | 7/2006 | Mongeon et al. |
| 2009/0306732 A1* | 12/2009 | Rosenberg et al. ............... 607/9 |

* cited by examiner

*Primary Examiner* — Alyssa M Alter

(57) ABSTRACT

Pacing related timing is determined for an implantable medical device (IMD) by pacing at an RV pacing site, a first LV pacing site and a second LV pacing site in accordance with a first site, a second site and a third site pacing order, and further in accordance with a first inter-electrode pacing delay between pacing at the first site and pacing at the second site and a second inter-electrode pacing delay between pacing at the second site and pacing at the third site. At least one of a sensed event or a paced event is detected for at each of the second site and the third site. The first inter-electrode pacing delay and the second inter-electrode pacing delay are adjusted to avoid sensed events in favor of paced events at each of the second site and the third site. An atrio-ventricular delay may also be adjusted to avoid sensed events or lack of capture due to possible fusion at the first site, in favor of paced events at the first site.

16 Claims, 9 Drawing Sheets

SYSTEMS AND METHODS FOR DETERMINING PACING RELATED PARAMETERS

BACKGROUND OF THE INVENTION

Embodiments of the present invention generally relate to cardiac stimulation devices and more particularly to systems and methods for determining pacing related parameters.

The normal electrical conduction of the heart allows electrical propagation to be transmitted from the sinoatrial node (SA) through both atria and forward to the atrioventricular node (AV). Normal physiology allows further propagation from the AV node to the ventricle or Purkinje Fibers and respective bundle branches and subdivisions. The SA and AV nodes stimulate the myocardium. Time ordered stimulation of the myocardium allows efficient contraction of all four chambers of the heart, thereby allowing selective blood perfusion through both the lungs and systemic circulation.

Implantable medical devices (IMDs) such as cardiac pacemakers or cardioverter defibrillators are used today for a variety of reasons to maintain an adequate heart rate. Recently, lead configurations have been introduced that include multiple electrodes located in, or proximate to, the left ventricle. IMDs are configured to monitor the electrical activity and pace in various chambers of a patient's heart. To do so, the IMD has a variety of operational parameters that can be adjusted to maintain desired cardiac function. Examples of such operational parameters are the delays between when combinations of electrodes deliver pacing pulses when no intrinsic event occurs, such as atrioventricular delay (hereinafter "AV delay"), right ventricle (RV) to left ventricle (LV) delay (hereinafter "RVLV delay" or "interventricular delay") or LV to LV delay (hereinafter: LVLV delay" or "intraventricular delay"), and the like. The proper setting of these delays establishes and maintains the desired cardiac function, and results in an improved hemodynamic response.

Heretofore, IMDs have afforded the clinician certain parameters to program. However, clinician programmed settings may not result in the desired hemodynamic performance in all patients or under conditions for a particular patient.

A need remains for a process to search automatically for certain pacing related parameters, such as AV delay, RV to LV delay, and/or LV to LV delay.

SUMMARY

The invention relates to systems and methods for determining pacing related timing of an implantable medical device (IMD). In one arrangement, pacing is provided at an RV pacing site, a first LV pacing site and a second LV pacing site in accordance with a first site, a second site and a third site pacing order, and further in accordance with a first inter-electrode pacing delay between pacing at the first site and pacing at the second site and a second inter-electrode pacing delay between pacing at the second site and pacing at the third site. At least one of a sensed event, i.e., intrinsic activation, or a paced event, i.e., evoked response or capture, is detected for at each of the second site and the third site. The first inter-electrode pacing delay and the second inter-electrode pacing delay are adjusted to avoid sensed events in favor of paced events at each of the second site and the third site. For example, in one aspect of the invention, the first inter-electrode delay is decreased when capture is not detected at the second site and the second inter-electrode delay is decreased when capture is not detected at the third site. In one arrangement, the first site is the RV pacing site, the second site is the first LV pacing site, and the third site is the second LV pacing site. In another arrangement, the first site is the first LV pacing site, the second site is the second LV pacing site, and the third site is the RV pacing site.

DETAILED DESCRIPTION

In the following detailed description, reference is made to the accompanying drawings which form a part hereof, and in which are shown by way of illustration specific embodiments in which the subject matter disclosed herein may be practiced. These embodiments, which are also referred to herein as "examples," are described in sufficient detail to enable those skilled in the art to practice the subject matter disclosed herein. It is to be understood that the embodiments may be combined or that other embodiments may be utilized, and that structural, logical, and electrical variations may be made without departing from the scope of the subject matter disclosed herein. The following detailed description is, therefore, not to be taken in a limiting sense, and the scope of the subject matter disclosed herein is defined by the appended claims and their equivalents. In the description that follows, like numerals or reference designators will be used to refer to like parts or elements throughout. In this document, the terms "a" or "an" are used, as is common in patent documents, to include one or more than one. In this document, the term "or" is used to refer to a nonexclusive or, unless otherwise indicated.

Figure 1A:
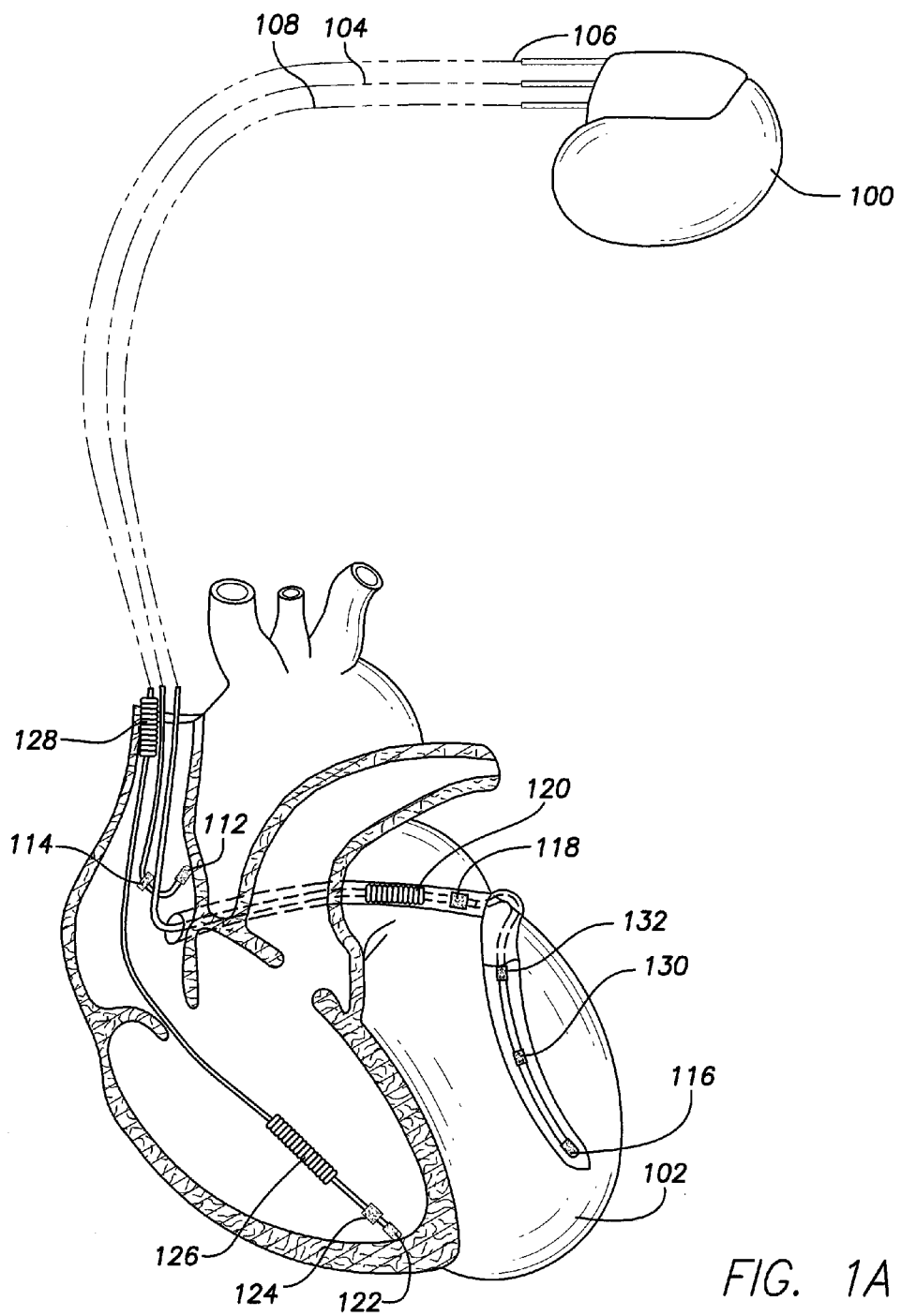
FIG. 1A is a simplified view of an exemplary implantable medical device (IMD) in electrical communication with at least three leads implanted in or on a patient's heart.

The concepts described herein are intended for implementation in a medical system that is configured or configurable to delivery cardiac therapy and/or sense information germane to cardiac therapy. With reference to FIG. 1A, one such medical system includes an implantable medical device (IMD) 100 and implantable leads 104, 106, 108 suitable for sensing cardiac activity and delivering multi-chamber therapy including cardioversion, defibrillation and pacing stimulation. The IMD 100 may be a cardiac pacemaker, an implantable cardioverter defibrillator (ICD), a cardiac resynchronization therapy (CRT) pacemaker, a cardiac resynchronization therapy defibrillator (CRT-D), and the like.

The IMD 100 is configured for placement in electrical communication with the right side of a patient's heart 102 by way of a right atrial (RA) lead 104 and a right ventricular (RV) lead 106. The RA lead 104 is designed for placement in a right atrium and, in this exemplary implementation, includes an atrial tip electrode 112, which typically is implanted in the patient's right atrial appendage, and an atrial ring electrode 114. Accordingly, the RA lead 104 is capable of sensing electrical cardiac signals, and delivering stimulation in the form of pacing therapy to the right side of the heart, and in particular the right atrium.

The RV lead 106, in this exemplary implementation, includes a RV tip electrode 122, a RV ring electrode 124, a RV coil electrode 126, and a superior vena cava (SVC) coil electrode 128. Typically, the RV lead 106 is designed to be transvenously inserted into the heart 102 to place the RV tip electrode 122 in the right ventricular apex, the RV coil electrode 126 in the right ventricle and the SVC coil electrode 128 in the superior vena cava. Accordingly, the RV lead 106 is capable of sensing electrical cardiac signals, and delivering stimulation in the form of pacing and shock therapy to the right side of the heart, and in particular the right ventricle.

The IMD 100 is in electrical communication with the left side of a patient's heart 102 by way of a coronary sinus (CS) lead 108 designed for placement in the coronary sinus region. As used herein the coronary sinus region refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The CS lead or LV lead 108, in this exemplary implementation is a quad-pole lead that includes a left ventricular (LV) tip electrode 116, a left atrial (LA) ring electrode 118, a LA coil electrode 120 and additional ring electrodes 130, 132 spaced apart between the tip electrode 116 and the coil electrode 120. Typically the CS lead 108 is designed to be transvenously inserted into the heart 102 to access the coronary sinus region so as to place the LV tip electrode 116 and additional ring electrodes 130, 132 adjacent to the left ventricle, and the (LA) ring electrode 118 and the LA coil electrode 120 adjacent to the left atrium. Accordingly, the CS lead 108 is capable of sensing electrical cardiac signals, and delivering stimulation in the form of pacing and shock therapy to the left side of the heart.

Although three leads are shown in FIG. 1A, fewer or more leads (with one or more pacing, sensing and/or shocking electrodes) may be used in order to efficiently and effectively provide pacing stimulation, cardioversion and/or defibrillation. Furthermore, an individual lead may include additional electrodes.

The IMD 100 monitors cardiac signals of the heart 102 to determine if and when to deliver stimulus pulses to one or more chambers of the heart 102. The IMD 100 may deliver pacing stimulus pulses to pace the heart 102 and maintain a desired heart rate and/or shocking stimulus pulses to treat an abnormal heart rate such as tachycardia or bradycardia.

The IMD 100 uses various combinations of electrodes for sensing the intrinsic cardiac activity and pacing by providing the minimum amount of energy (both volts and pulse width) required to reliably depolarize the cardiac chamber. Electrodes are selected to provide sensed electrogram waveforms from three chambers: the RA, the RV and the LV. The electrograms are sensed along various cardiac vectors between the RA, the RV and the LV based on which electrodes are chosen. The deflection of the electrocardiograph from ground is proportional to the component size of the cardiac vector in the direction of the lead. These measurements are used to calculate cardiac pacing.

Figure 1B:
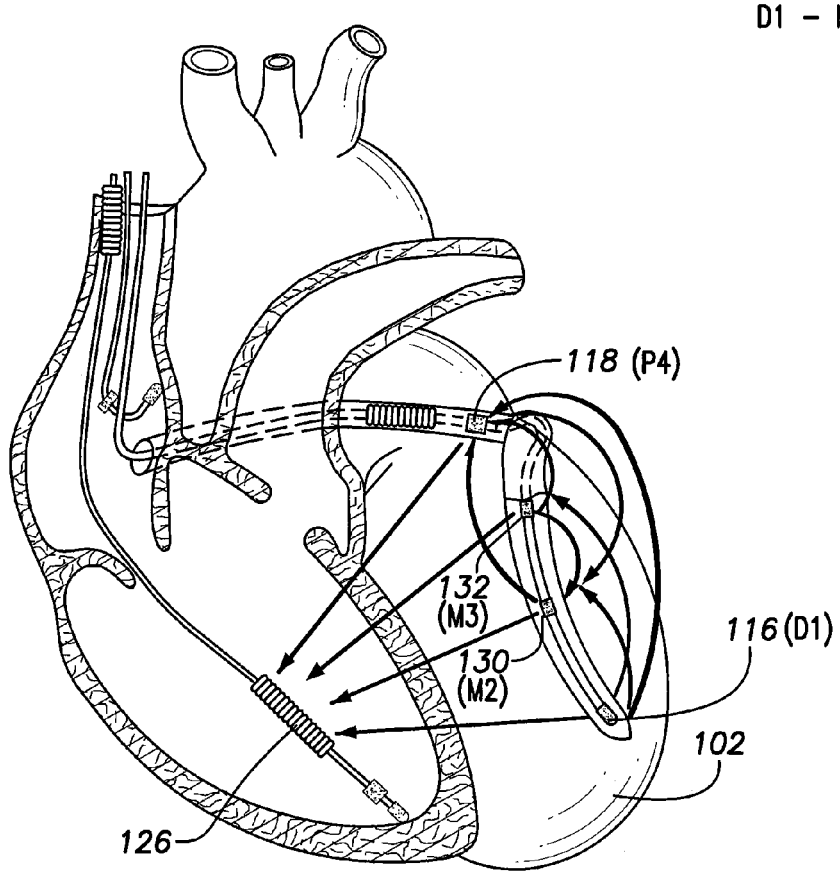
FIG. 1B illustrates exemplary cardiac vectors available with a right ventricular (RV) lead and a left ventricular (LV) quad-pole lead.

FIG. 1B illustrates quad-pole left ventricular cardiac vectors. The RV coil electrode 126 may be used either for pacing or for sensing electrical cardiac signals at the RV. For example, the RV coil electrode 126 may be used to obtain cardiac signals associated with a pacing site. For example, the RV coil electrode 126 may be used to pace in the RV.

As illustrated in FIG. 1B the LV lead 108 has four LV electrodes 116, 130, 132, 118 (hereinafter "quad-pole"), further identified by respective positions—distal 1 (D1), middle 2 (M2), middle 3 (M3) and proximal 4 (P4). Optionally, the LV lead 108 may have any number of LV electrodes and any combination of such electrodes may be utilized to form sensing and/or pacing vectors. The ventricular pulse generator 240 (FIG. 2) generates stimulation pulses through the one or more electrodes 116, 130, 132, 118 along desired vectors formed between various pairs of electrodes selected among the four LV electrodes and the RV coil electrode 126. A vector is a force that has magnitude, direction, and polarity. The various vectors are depicted by an arrow signifying the polarity of a pacing or sensing configuration and are listed in the figure. Optionally, the polarity for pacing or sensing may be switched for one or more of the vectors.

Figure 2:
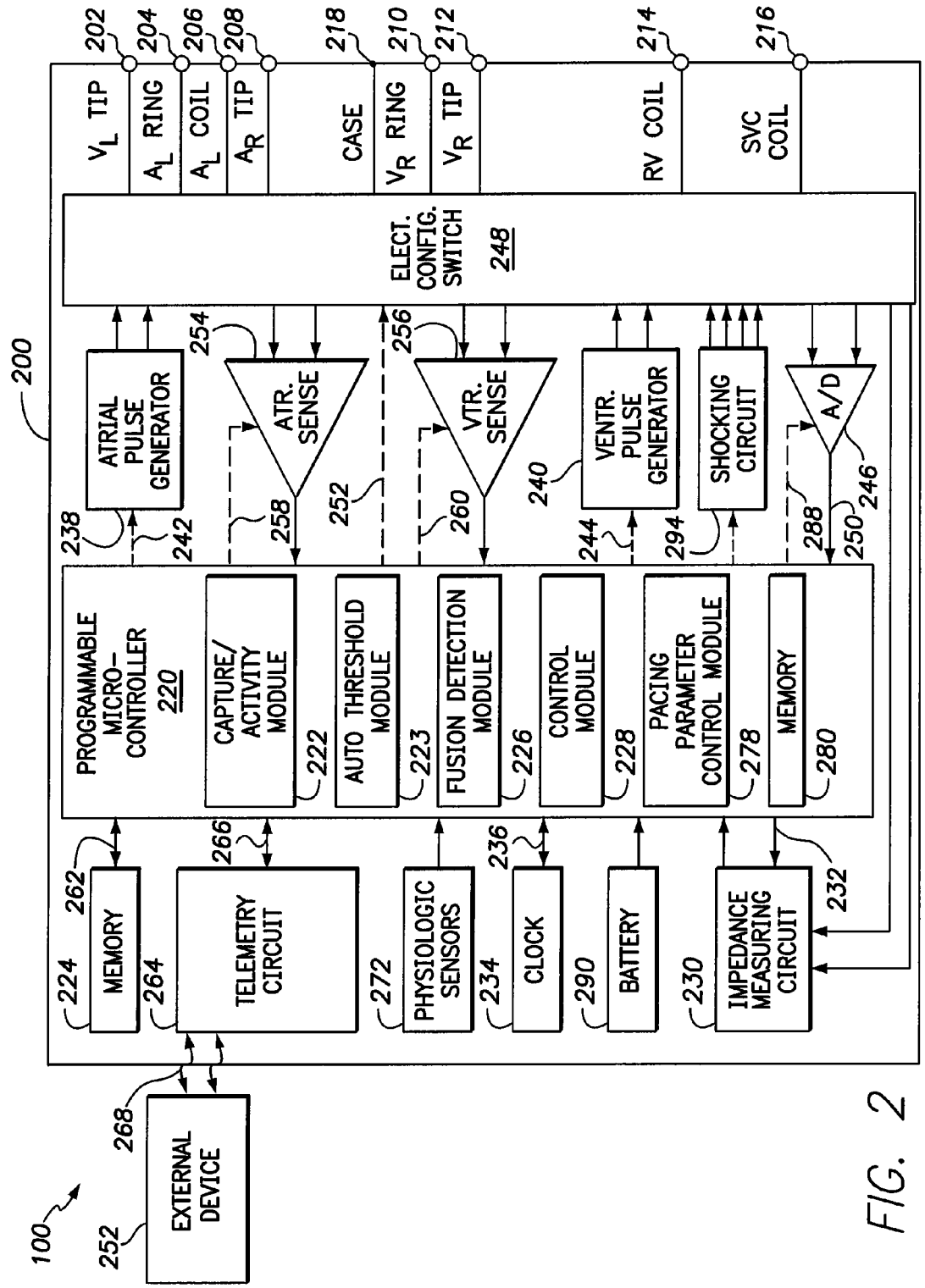
FIG. 2 is a functional block diagram of the IMD of FIG. 1A.

FIG. 2 illustrates a block diagram of exemplary internal components of the multi-chamber IMD 100 shown in FIG. 1A. While a particular multi-chamber device is shown, the multi-chamber device is for illustration purposes only, and one of ordinary skill in the pertinent art could readily duplicate, eliminate or disable the appropriate circuitry in any desired combination to provide a device capable of treating the appropriate chamber(s) with cardioversion, defibrillation, and/or pacing stimulation.

The IMD 100 includes a housing 200 that includes a left ventricle tip input terminal ($V_L$ TIP) 202, a left atrial ring input terminal ($A_L$ RING) 204, a left atrial coil input terminal ($A_L$ COIL) 206, a right atrial tip input terminal ($A_R$ TIP) 208, a right ventricular ring input terminal ($V_R$ RING) 210, a right ventricular tip input terminal ($V_R$ TIP) 212, a RV coil input terminal 214 and an SVC coil input terminal 216. A case input terminal 218 may be coupled with the housing 200 of the IMD 100. The input terminals 202-218 may be electrically coupled with the electrodes 112-128 (shown in FIG. 1B). Additional input terminals (not shown) may be included as necessary to provide for connection with additional electrodes, such as LV ring electrodes 130, 132.

The IMD 100 includes a programmable microcontroller 220, which controls the operation of the IMD 100. The microcontroller 220 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. The microcontroller 220 may include one or more modules and processors configured to perform one or more of the operations described above in connection with the FIG. 1B.

A capture/activity module (CAM) 222 performs capture confirmation tests by sensing for evoked responses of the heart 102 following delivery of stimulus pulses to the heart. For example, CAM 222 may examine the waveforms of cardiac signals sensed after supplying a stimulus pulse to an atrium or ventricle of the heart 102 to detect for cardiac depolarization waveforms, e.g., P waves or R waves, indicative of capture. In accordance with one embodiment, once a pacing pulse is delivered at a RV or LV pacing site, the CAM 222 senses for cardiac signals at the same RV or LV pacing site where the pacing pulse was delivered. In one embodiment, the CAM 222 determines, from the sensed cardiac signals, whether the pacing pulse achieved capture of the surrounding local tissue. Such determination may be made based on detected voltage/threshold comparisons or other morphology analyses known in the art. In one embodiment, the CAM 222 also monitors cardiac waveforms for intrinsic activity, i.e., cardiac depolarizations resulting from naturally conducted activation through the myocardium. The operation of CAM 222 is discussed below in more detail in connection with FIGS. 3-5.

An autothreshold module 223 performs threshold searches when the IMD 100 operates in the autothreshold mode. For example, the autothreshold module 223 may incrementally decrease the electrical potential of stimulus pulses delivered to myocardium of the heart until a loss of capture is detected in a first predetermined number of consecutive cardiac cycles. The autothreshold module 223 then may incrementally increase the electrical potential of the stimulus pulses until capture is detected in a second predetermined number of consecutive cardiac cycles.

A fusion detection module 226 identifies fusion-based behavior in myocardium of the heart 102. Fusion beats or fusion events are myocardial activations induced by simultaneous occurrence of an intrinsic depolarization and pacing pulse delivery. The fusion detection module 226 tracks the fusion beat count and the total beat count during the time period that the IMD 100 operates in each of the autocapture and autothreshold modes. A control module 228 automatically switches the IMD 100 between the autothreshold and autocapture modes based on the presence of fusion-based behavior detected by the fusion detection module 226.

A pacing parameter control module (PCM) 278 is designed to interface with the RA, the RV, and the LV electrodes for sensing and pacing in the corresponding cardiac chamber. The PCM 278 may perform repolarization and depolarization measurements to calculate, inter alia, AV timing optimization, V-V timing optimization, multisite CRT AV timing optimization, multisite CRT V-V timing optimization, global dispersion of repolarization, and multisite electrode site selection. Further, the PCM 278 may be programmed to optimize pacing based on global activation and repolarization, reflecting overall myocardial properties. Optionally, the PCM 278 may also be programmed to correct for transmural and LV endocardial conduction anomalies. The PCM 278 may perform pacing optimization and correction of transmural and LV endocardial conduction anomalies by pacing at one or more sites of a multi-polar electrode lead. Alternatively, the PCM 278 may be programmed to reduce activation/repolarization dispersion as a basis for device-based optimization.

The PCM 278, in accordance with one embodiment, determines pacing related timing delays—including AV delays, RVLV delays and LVLV delays—of an implantable medical device (IMD) 100. These delays represent the time delay between deliveries of pacing pulses at the multiple pacing sites and are at times referred to herein as inter-electrode delays. The PCM 278 is configured to obtain cardiac signals associated with a number of ventricular pacing sites, including in one configuration a RV pacing site and at least one of multiple LV pacing sites. After obtaining cardiac signals associated with a RV, the PCM 278 directs the ventricular pulse generator 240 to deliver pacing pulses at the RV pacing site and at, at least one of the LV pacing sites when desired intrinsic events are not sensed from the cardiac signals. Additionally, the PCM 278 is configured to adjust pacing delays in response to capture confirmation and intrinsic activity tests performed by the CAM 22.

The PCM 278 may further be configured to repeat adjusting operations to perform a search for an outer limit for an inter-electrode delay. In one configuration, the PCM 278 provides sequential pacing pulses to three different ventricular sites defined by three different pacing vectors. In one example, pacing pulses are provided first at a first LV pacing site (LV1), next at a second LV pacing site (LV2) and next at an RV pacing site (RV) with respective inter-electrode delays LV1LV2 and LV2RV there between that are adjusted in the adjusting operation. In another example, the pacing pulses may be provided to the RV site first, the LV1 site second and the LV2 site last and the respective inter-electrode delays are RVLV1 and LV1LV2.

The microprocessor 220 receives signals from electrodes via an analog-to-digital (ND) data acquisition system 246. The cardiac signals are sensed by the electrodes and communicated to the data acquisition system 246. The cardiac signals are communicated through the input terminals 202-216 to an electronically configured switch bank, or switch, 248 before being received by the data acquisition system 246. The data acquisition system 246 converts the raw analog data of the signals obtained by the electrodes into digital signals 250 and communicates the signals 250 to the microcontroller 220. A control signal 288 from the microcontroller 220 determines when the data acquisition system 246 acquires signals, stores the signals 250 in the memory 280, or transmits data to an external device 252.

An atrial pulse generator 238 and ventricular pulse generator 240 generate stimulation pulses for delivery by the RA lead 104, the RV lead 106, and/or the coronary sinus lead 108 via a switch 248. The atrial pulse generator 238 and the ventricular pulse generator 240 are generally controlled by the microcontroller 220 via appropriate control signals 242 and 244, respectively, to trigger or inhibit the stimulation pulses.

The switch 248 includes a plurality of switches for connecting desired electrodes and input terminals 202-218 to the appropriate I/O circuits. The switch 248 closes and opens switches to provide electrically conductive paths between the circuitry of the IMD 100 and the input terminals 202-218 in response to a control signal 282. An atrial sensing circuit 254 and a ventricular sensing circuit 256 may be selectively coupled to the leads 104-108 of the IMD 100 through the switch 248 for detecting the presence of cardiac activity in the chambers of the heart 102. The sensing circuits 254, 256 may sense the cardiac signals that are analyzed by the microcontroller 220. Control signals 258, 260 from the microcontroller 220 direct output of the sensing circuits 254, 256 that are connected to the microcontroller 220. An impedance measuring circuit 230 may be enabled by the microcontroller 220 via a control signal 232. The impedance measuring circuit 230 may be electrically coupled to the switch 248 so that an impedance vector between any desired pairs of electrodes 120-128 may be obtained. The IMD 100 additionally includes a battery 270 that provides operating power to the circuits shown within the housing 200, including the microcontroller 220. The IMD 100 includes a physiologic sensor 272 that may be used to adjust pacing stimulation rate according to the exercise state of the patient. The IMD 100 includes a shocking circuit 274.

A clock 234 may measure time relative to the cardiac cycles or cardiac signal waveforms of the heart 102. The clock 234 measures elapsed amounts of time based on start and stop control signals 236 from the microcontroller 220 to determine the ventricular and atrial heart rates. Additionally, the clock 234 may track the amount of time elapsed between threshold searches. The elapsed time may be compared to a predetermined time period to determine whether to perform another threshold search.

The program micro-controller 220 directs delivery of paces to promote AV synchrony and good hemodynamic function, and may do so in concert with the clock 234. For example, the program micro-controller 220 controls the duration of an AV delay, and that determines whether IMD 100 operates in a pacing mode or a search AV delay mode.

The IMD 100 may sense the R-R interval, i.e., the interval between ventricular activations, via atrial sensing circuit 254 and a ventricular sensing circuit 256. The R-R interval is directly related to the rate at which heart 102 beats. For example, the heart rate, alone or in concert with another physiological signal, may be used as a parameter for changing the AV delay.

The IMD 100 may lengthen or shorten the AV delay in response to a condition as described below. For example, IMD 100 may adjust the AV delay in response to activity sensed atrial sensing circuit 254 and a ventricular sensing circuit 256. The invention is not limited to an IMD, but may be applied by any device that may be used to calculate an AV delay as well.

In one embodiment, the IMD 100 performs a multi-pole optimization based on cardiac signals sensed using the leads 104, 106, 108. In another embodiment, the IMD 100 transmits the cardiac signals to an external programmer that performs the optimization. That is, the device programmer determines optimal multi-pole ventricular pacing parameters, which are then programmed into the IMD 100 via telemetry. Other external devices might instead be used to perform the optimization, such as bedside monitors or the like.

The memory 224 may be embodied in a computer-readable storage medium such as a ROM, RAM, flash memory, or other type of memory. The microcontroller 220 is coupled to the memory 224 by a suitable data/address bus 262. The memory 224 may store programmable operating parameters and thresholds used by the microcontroller 220, as required, in order to customize the operation of IMD 100 to suit the needs of a particular patient. For example, the memory 224 may store the safe mode parameters used to switch the active parameters of the IMD 100 prior to a medical procedure. In another example, the memory 224 may store data indicative of cardiac signal waveforms, the fusion thresholds, predetermined time periods, fusion beat counts, total beat counts, and the like.

The safe mode parameters of the IMD 100 may be non-invasively programmed into the memory 224 through a telemetry circuit 264 in communication with the external device 252, such as a trans-telephonic transceiver or a diagnostic system analyzer. For example, the external device that telemetry circuit communicates with may be a non-programming activation device. The telemetry circuit 264 may be activated by the microcontroller 220 by a control signal 266. The telemetry circuit 264 allows intra-cardiac electrograms, cardiac waveforms of interest, detection thresholds, status information relating to the operation of IMD 100, and the like, to be sent to the external device 252 through an established communication link 268.

Figure 3:
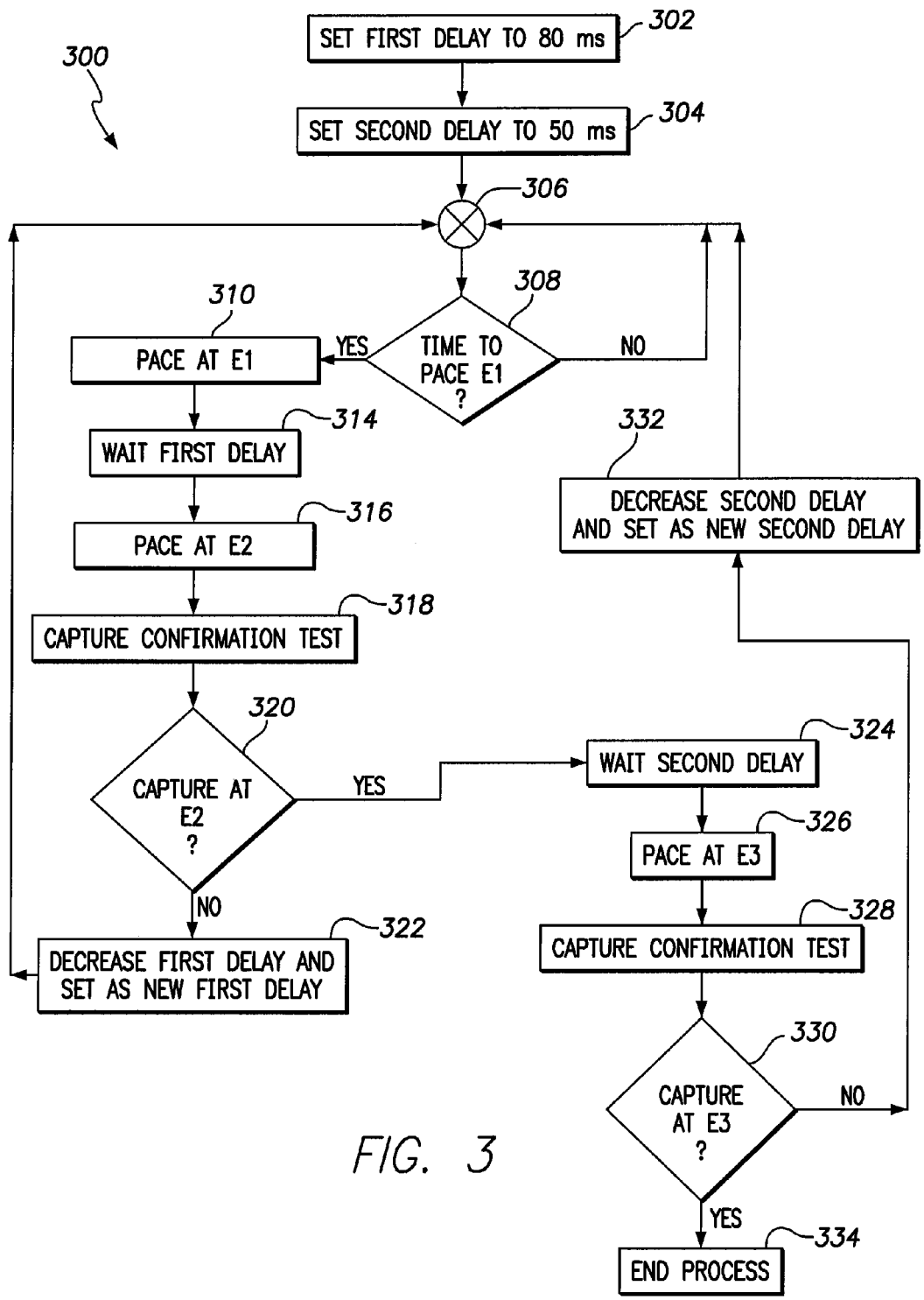
FIG. 3 illustrates a process to adjust pacing delay between electrodes based on capture confirmation.
Figures 1, 4:
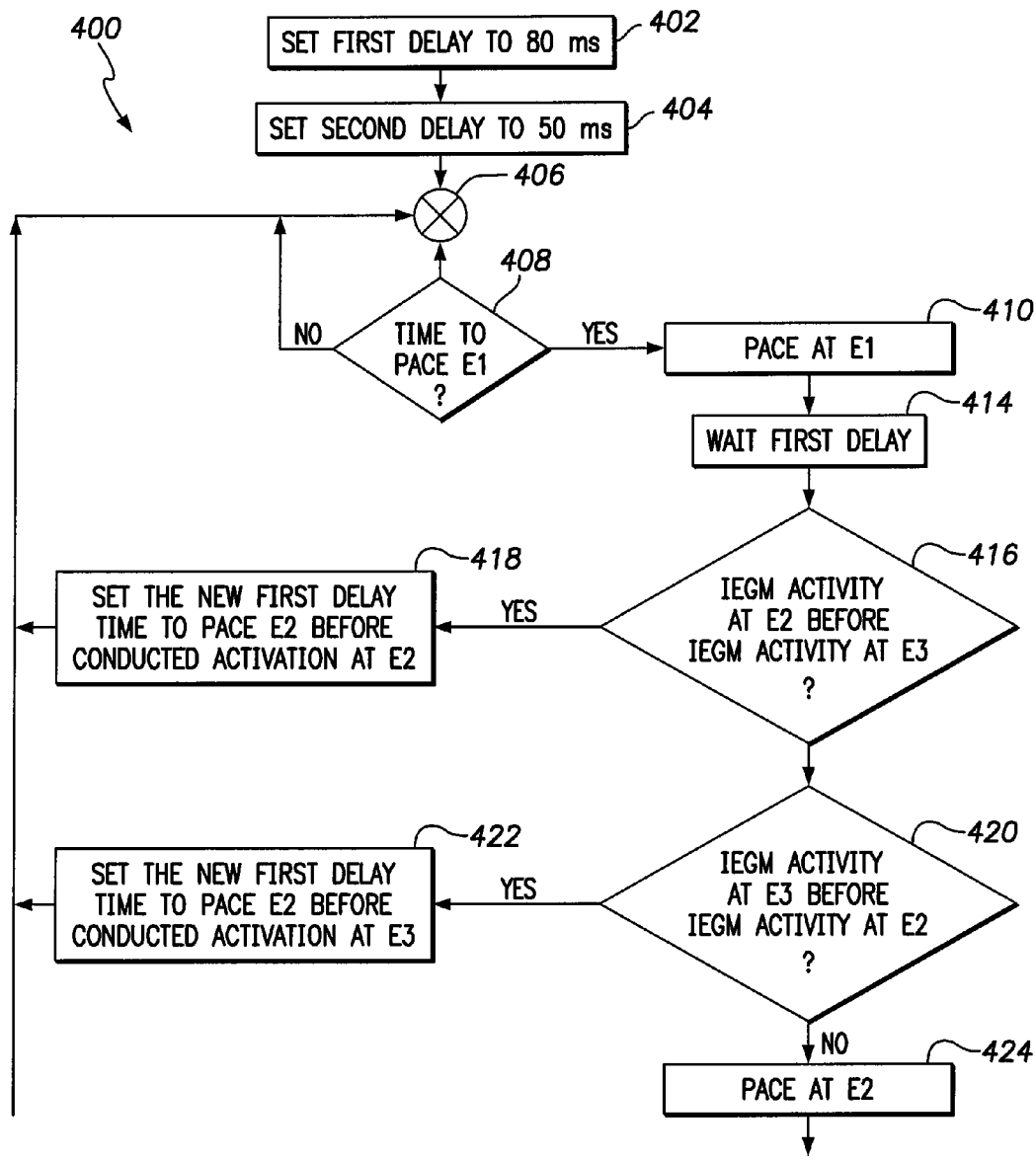
FIG. 4 illustrates a process to adjust pacing delay between electrodes based on order of detected intracardiac electrogram (IEGM) activity.
Figures 2, 4:
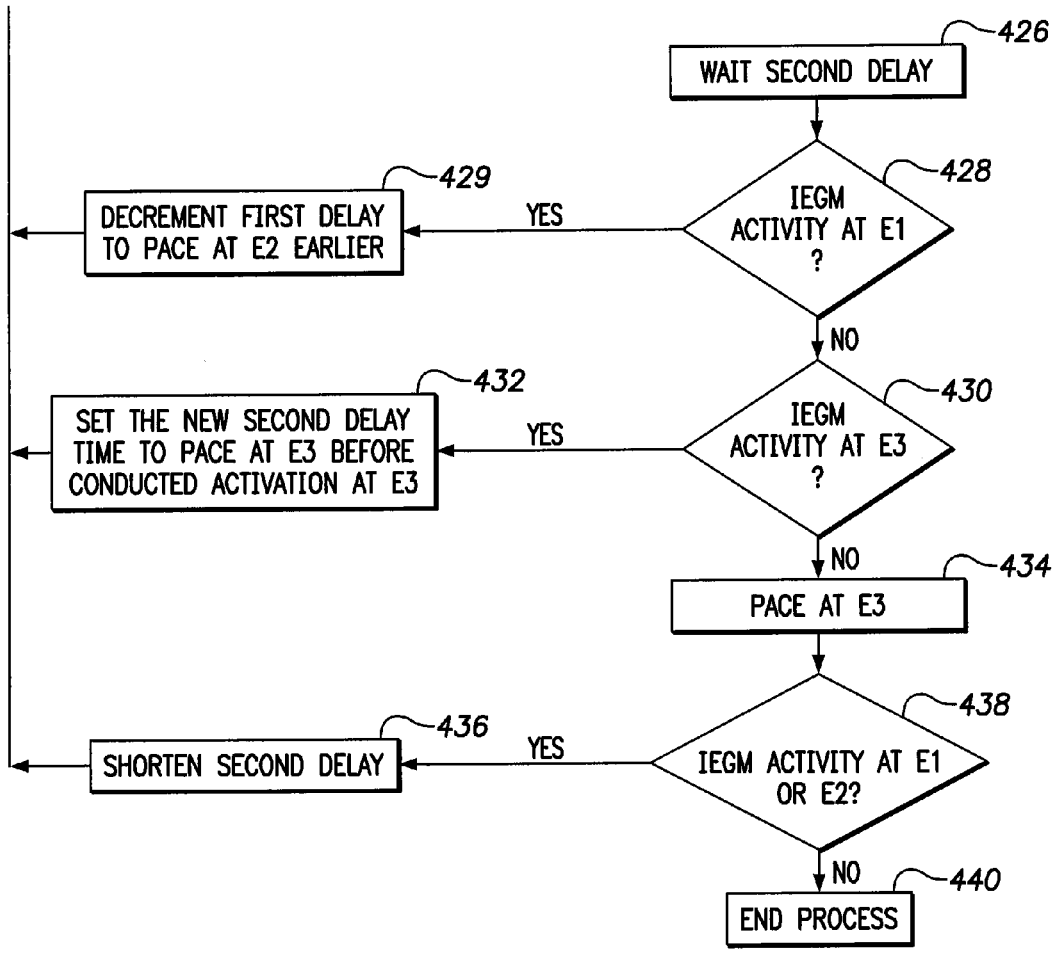

Throughout the discussion of FIGS. 3-5, ventricular electrodes are referred to using the terms E1, E2, E3, etc. There may be more than three electrodes, such as when using a multi-pole LV lead or otherwise. The particular ventricular pacing sites associated with the ventricular electrodes E1, E2, E3, etc. will vary depending upon i) the combination or types of leads used, ii) the mode of operation and iii) the therapy.

In general, the processes 300, 400, and 500 comprise pacing from a first site of three different ventricular pacing sites, sensing for intrinsic activity at both of the ventricular pacing sites that were not paced from, and determining which of these two sites first experienced intrinsic activity. The process sets an inter-electrode delay to pace first from the one of the two sites that first experienced intrinsic activity. In addition, the processes 300, 400, 500 may determine an order in which the multiple LV pacing sites experience intrinsic activity following an initial paced or intrinsic event, and then adjust an inter-electrode delay such that pacing pulses are delivered from the multiple LV pacing sites in the order in which the multiple LV pacing sites experience intrinsic activity. The processes 300, 400, and 500, may search for the inter-electrode delay, by starting with a maximum allowable inter-electrode delay and recursively decreasing the maximum inter-electrode delay to determine the final inter-electrode delay, or by starting with a minimum delay and recursively increasing the delay.

FIG. 3 illustrates a process to set pacing delays between electrodes based on capture confirmation. In the example of FIG. 3, the IMD 100 is configured to pace from a RV pacing site (RV), a first LV pacing site (LV1), and a second LV pacing site (LV2). "Paced events" are myocardial activations induced by pacing stimuli, such as electrical pulses, that are provided to the heart to cause depolarizations. Paced events are referred to as evoked responses or capture. "Sensed events" are intrinsic activations (or depolarizations) resulting from natural conduction through the myocardium. Sensed events are not induced by pacing stimuli. "Fusion events" are myocardial activations induced by simultaneous occurrence of an intrinsic depolarization and pacing pulse delivery. Paced events, sensed events and fusion events (sometimes referred to herein as "lack of capture" or "failure to capture") are detected for through analysis of cardiac activity signals (IEGMs) obtained from electrodes.

The IMD 100 staggers the timing between when pacing pulses are delivered at the RV pacing site, the first LV pacing site and the second LV pacing site, through respectively placed electrodes. The timing associated with the RV pacing site, the first LV pacing site and the second LV pacing site are programmable as two independent programmable delays, i.e., inter-electrode delays. In one example, the IMD 100 is sequenced to pace first at the first LV pacing site, next at the second LV pacing site and finally at the RV pacing site with respective delays. Alternatively, the IMD 100 may be sequenced to pace first at the RV pacing site, next at the first LV pacing site and finally at the second LV pacing site with respective inter-electrode delays.

The process 300 starts by setting a maximum first inter-electrode delay at 302. For example, the first inter-electrode delay may represent the interval between delivering a pacing pulse at the RV pacing site and a pacing pulse at the first LV pacing site (RVLV1 delay). Alternatively, the first inter-electrode delay may represent the interval between delivering a pacing pulse at the first LV pacing site and a pacing pulse at the second LV pacing site (LV1 LV2 delay). In one embodiment, the predetermined maximum first inter-electrode delay may be 80 milliseconds (ms). Alternatively, the maximum first inter-electrode delay value may be determined by a clinician.

At 304, a maximum second inter-electrode delay is set. For example, in the case where the first inter-electrode delay is an RVLV1 delay, the second inter-electrode delay may represent the interval between delivering a pacing pulse at the first LV pacing site and a pacing pulse at the second LV pacing site (LV1LV2 delay). Alternatively, in the case where the first inter-electrode delay is an LV1LV2 delay, the second inter-electrode delay may represent the interval between delivering a pacing pulse at the second LV pacing site and a pacing pulse at the RV pacing site (LV2RV delay). In one embodiment, the predetermined maximum second inter-electrode delay interval may be 50 ms. Alternatively, the maximum second inter-electrode delay value may be determined by a clinician. For example, the external programmer device 252 may be used to program the maximum first and the maximum second inter-electrode delay intervals. Alternatively, the maximum first and the maximum second inter-electrode delay interval may be set by the manufacturer of the IMD 100.

At 308, the process 300 determines when to pace at a first ventricular electrode (E1). For example, the first electrode may correspond to the RV pacing site (RV). Alternatively, the first electrode may correspond to the first LV pacing site (LV1). If it is not yet the time to pace at the first electrode E1, the flow moves to junction 306 and the process 300 recursively performs step 308 until it is time to pace. For example, the decision at 308 may yield a "NO" answer, when intrinsic beats are detected in one or both ventricles. The decision at 308 may yield a "YES" answer, when no intrinsic beat occurs in the RV within an AV delay following a sensed event or paced event in the RA. When it is time to pace, a pacing pulse is delivered at the first electrode E1 and the flow moves along 310.

At 314, the flow pauses for the first inter-electrode delay. At the end of the first inter-electrode delay, the IMD 100 applies a pacing pulse at the second electrode E2 (at 316). For example, in the case where the first electrode corresponds to the RV pacing site (RV), the second electrode E2 may correspond to the first LV pacing site (LV1). Alternatively, in the case where the first electrode corresponds to the first LV pacing site (LV1), the second electrode E2 may correspond to the second LV pacing site (LV2). Following the second pacing pulse, the IMD 100 performs a capture confirmation test 318 at the second electrode E2. Preferably, pacing is done throughout the present process at stimulus levels that avoid lack of capture due to insufficient energy. Therefore, when capture confirmation fails, it is not attributed to insufficient energy and instead likely due to either pacing into a refractory period associated with intrinsic conduction, or pacing nearly simultaneous with intrinsic activation so as to result in fusion.

At 320, the process 300 checks whether there was an evoked response, i.e., capture at the second electrode E2, in response to the pacing pulse delivered at the second electrode E2. If there was no capture at the second electrode E2, the first inter-electrode delay value is decreased 322.

Returning to 320, when capture at the second electrode E2 is confirmed, the flow moves to 324. The process pauses for the second inter-electrode delay 324. Next, at 326, the IMD 100 provides a pacing pulse at the third electrode E3. For example, in the case where the second electrode E2 corresponds to the first LV pacing site (LV1), the third electrode E3 may correspond to second LV pacing site (LV2). Alternatively, in the case where the second electrode E2 corresponds to the second LV pacing site (LV2), the third electrode E3 may correspond to the RV pacing site (RV). Following pacing at the third electrode E3, the process 300 performs another capture confirmation test at 328. At 330, if an evoked response, i.e., capture, is not confirmed following the pacing pulse delivered at the third electrode E3, the flow moves to 332. At 332, the second inter-electrode delay is decreased and the flow moves to junction 306. The loop (306 to 332) is performed until capture is confirmed in response to the pacing pulse delivered at the third electrode E3. Returning to 330, if capture is confirmed, the process ends at 334.

The amount of reduction in the first and second inter-electrode delays may be a preset value used for each iteration. Alternatively, the amount of reduction in the first and second inter-electrode delay may be calculated for every iteration of the loop based on other parameter settings, based on measured cardiac signals (e.g., RR interval), and the like. Optionally, the operations at 322 and 332 may be set in a different manner, not simply a linear decreasing manner. For example, other search algorithms may be used such as a bi-section method, a Newton method and the like.

FIG. 4 illustrates a process to set inter-electrode pacing delays between three electrodes located at ventricular pacing sites, based on order of intracardiac electrogram (IEGM) activity detected at one or more of the sites, so as to avoid conducted activation between the electrodes. The three ventricular pacing sites include an RV pacing site (RV), a first LV pacing site (LV1) and a second LV pacing site (LV2). A first inter-electrode delay may be between delivering pacing pulses at the RV pacing site and a first LV pacing site (RVLV1 delay). Alternatively, a first inter-electrode delay may represent an interval between delivering a pacing pulse at a first LV pacing site and a pacing pulse at a second LV pacing site (LV1LV2 delay). In the case where the first inter-electrode delay is an RVLV1 delay, a second inter-electrode delay may represent an interval between delivering a pacing pulse at a first LV pacing site and a pacing pulse at a second LV pacing site (LV1LV2 delay). Alternatively, in the case where the first inter-electrode delay is an LV1LV2 delay, the second inter-electrode delay may represent an interval between delivering a pacing pulse at a second LV pacing site and a pacing pulse at a RV pacing site (LV1LV2 delay).

In one example, the IMD 100 is sequenced to pace first at the first LV pacing site (LV1), next at the second LV pacing site (LV2) and finally at the RV pacing site (RV) with respective delays. Alternatively, the IMD 100 is sequenced to pace first at the RV pacing site (RV), next at the first LV pacing site (LV1) and finally at the second LV pacing site (LV2) with respective delays.

The process 400 starts by setting a maximum first inter-electrode delay at 402. For example, the first inter-electrode delay is the interval between delivering a pacing pulse at the RV pacing site and a pacing pulse at the first LV pacing site (RVLV1 delay). Alternatively, the first inter-electrode delay is the interval between delivering a pacing pulse at the first LV pacing site and a pacing pulse at the second LV pacing site (RVLV1 delay). In one embodiment, the predetermined maximum first inter-electrode delay may be 80 ms. Alternatively, the maximum first inter-electrode delay value may be determined by a clinician.

At 404, a maximum second inter-electrode delay is set. For example, in the case where the first inter-electrode delay is an RVLV1 delay, the second inter-electrode delay may represent the interval between delivering a pacing pulse at the first LV pacing site and a pacing pulse at the second LV pacing site (LV1LV2 delay). Alternatively, in the case where the first inter-electrode delay is an LV1LV2 delay, the second inter-electrode delay may represent the interval between delivering a pacing pulse at the second LV pacing site and a pacing pulse at the RV pacing site (LV2RV delay). In one embodiment, the maximum second inter-electrode delay interval may be 50 ms. Alternatively, the maximum second inter-electrode delay value may be determined by a clinician. For example, the external programmer device 252 may be used to program the maximum first and the maximum second inter-electrode delay intervals. Alternatively, the maximum first and the maximum second inter-electrode delay interval may be set by the manufacturer of the IMD 100.

At 408, the process 400 determines when to pace at a first ventricular electrode E1. For example, the first electrode may correspond to the RV pacing site (RV). Alternatively, the first electrode may correspond to the first LV pacing site (LV1). If it is not yet the time to pace at the first electrode E1, the flow moves to junction 406 and the process 400 recursively performs step 408 until it is time to pace. For example, the decision at 408 may yield a "NO" answer, when intrinsic beats are detected in one or both ventricles. The decision at 408 may yield a "YES" answer, when no intrinsic beat occurs in the RV within an AV delay following an sensed event or paced event in the RA. When it is time to pace, a pacing pulse is delivered at the first electrode E1 (410) At 414, the process 400 pauses for the duration of the first inter-electrode delay.

At 416, the process determines whether cardiac activity, i.e., conducted activation through the myocardium originating from the paced event at electrode E1, is sensed by the second electrode E2 before the cardiac activity is sensed by the third electrode E3. This cardiac activity may be sensed using an intracardiac electrogram (IEGM) obtained through electrode E2 and electrode E3, and accordingly may be referred to herein as "IEGM activity." When the second electrode E2 senses IEGM activity before the third electrode E3, the flow moves to 418 where a new first inter-electrode delay time is set. For example, when a pacing pulse is delivered at the first electrode E1, the pacing pulse propagates in every direction. The second electrode E2 will sense the pacing event from the first electrode E1 at some point in time. The IMD 100 may calculate the time taken by the pacing pulse to propagate from the first electrode E1 to the second electrode E2. The new first inter-electrode delay time may be set so that pacing occurs at the second electrode E2 before the conducted activation, which originated from the pacing event at first electrode E1, reaches the second electrode E2. The flow moves back to a junction 406. The loop (406 to 416) is repeated until no IEGM activity is detected at the second electrode E2 before the IEGM activity is detected at the third electrode E3 in response to the pacing event at first electrode E1.

Returning to 416, when IEGM activity is not sensed at the second electrode E2 before the IEGM activity at the third electrode E3, the flow moves to 420. At 420, the process determines whether IEGM activity is detected at the third electrode E3 before the IEGM activity is detected at the second electrode E2 in response to the pacing event at the first electrode E1. When IEGM activity is detected at the third electrode E3 before IEGM activity at the second electrode E2, a new first inter-electrode delay value is set at 422. The new first inter-electrode delay value may be set in order that pacing occurs at the second electrode E2 before the conducted activation from the pacing event at the first electrode E1 reaches the third electrode E3. The flow moves back to the junction 406. The loop (406 to 420) is executed until no IEGM activity is detected at the third electrode E3 before IEGM activity is detected at the second electrode E2 in response to the pacing event at the first electrode E1.

When no IEGM activity is detected at the third electrode E3 before the IEGM activity at the second electrode E2, the IMD 100 provides a pacing pulse at the second electrode E2 (424). Following the paced event at the second electrode E2, the process 400 pauses for the duration of the second inter-electrode delay 426. At 428, the process determines whether there is IEGM activity at the first electrode E1 following the pacing event at the second electrode E2. When IEGM activity appears at the first electrode E1 after the pacing event on the second electrode E2, this indicates that potential retrograde conduction is occurring from electrode E2 back to electrode E1 because the tissue at electrode E1 is no longer refractory. To avoid this problem, a pacing pulse should be delivered at E2 closer in time following the pacing pulse delivered at E1. Hence, when the test at 428 is YES, flow moves to 429.

At 429, the first delay is decreased so that a pacing pulse will be delivered at the second electrode E2 sooner after the pacing pulse is delivered at the first electrode E1. When the test at 428 is NO, flow moves to 430. At 430, the process 400 determines whether IEGM activity is detected at the third electrode E3 following the pacing pulse at electrode E2. When IEGM activity is detected at the third electrode E3, the flow moves to 432. At 432, a new second inter-electrode delay value is set. The new second inter-electrode delay value is set so as to provide a pacing pulse at the third electrode E3 before the conducted activation from the paced event at the second electrode E2 is received at the third electrode E3. The flow moves back to the junction 406. The loop (406 to 430) is repeated until no IEGM activity is detected at the third electrode E3. Returning to 430, when no IEGM activity is detected at the third electrode E3, the flow moves to 434.

At 434, a pacing pulse is delivered at the third electrode E3. Next, at 438, the process determines whether IEGM activity is detected at electrode E1 or electrode E2 as a result of the pacing pulse delivered from the third electrode E3. If so, this indicates that the second inter-electrode delay (between E2 and E3) may be too long. Therefore, flow moves to 436 where the second inter-electrode delay is shortened. After 436, flow returns to 406. The process of 406 to 436 is repeated until there is no IEGM activity on E1 or E2 (at 438) following pacing at E3. When the test at 438 is NO, flow moves to 440 and the process ends.

Figure 5A:
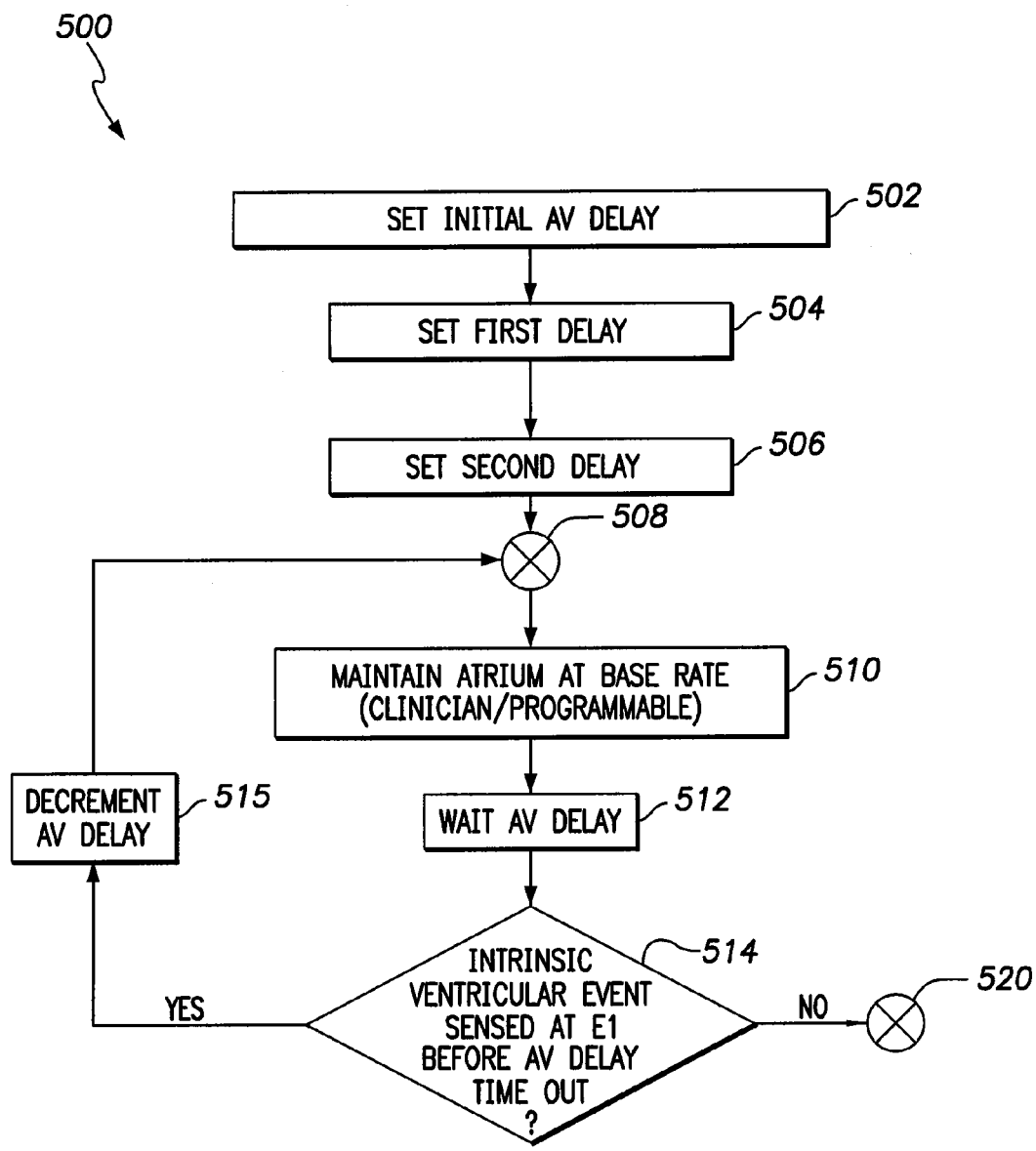
FIGS. 5A-5C together illustrate a process to search for an AV delay.

FIG. 5A illustrates an initial part of a process that searches for an AV delay along with first and second inter-electrode delays, respectively either of an RVLV delay, e.g., interventricular delay, or an LVLV delay, e.g., intraventricular delay. The process 500 starts at 502 by setting a predetermined AV delay. For example, the maximum predetermined AV delay may be an AV delay such as 240 ms. Next, the process 500 sets a predetermined first inter-electrode delay (e.g., a maximum, 80 ms). For example, the first inter-electrode delay may represent the interval between delivering a pacing pulse at an electrode associated with an RV pacing site and a pacing pulse at an electrode associated with a first LV pacing site (RVLV1 delay). Alternatively, the first inter-electrode delay may represent the interval between delivering a pacing pulse at the first LV pacing site and a pacing pulse at an electrode associated with a second LV pacing site (LV1LV2 delay). The first inter-electrode delay may be a predetermined delay (e.g., 80 ms), determined by a clinician, or obtained from the processes described with reference to FIGS. 3 and 4.

At 506, the process 500 involves setting a maximum second inter-electrode delay. For example, in the case where the first inter-electrode delay is an RVLV1 delay, the second inter-electrode delay may represent the interval between delivering a pacing pulse at the first LV pacing site and a pacing pulse at the second LV pacing site (LV1LV2 delay). Alternatively, in the case where the first inter-electrode delay is an LV1LV2 delay, the second inter-electrode delay may represent the interval between delivering a pacing pulse at the second LV pacing site and a pacing pulse at the RV pacing site (LV2RV delay). In one embodiment, the maximum second inter-electrode delay interval may be 50 ms. Alternatively, the maximum second inter-electrode delay value may be determined by a clinician. For example, the external programmer device 252 may be used to program the maximum first and the maximum second inter-electrode delay intervals. Alternatively, the maximum first and the maximum second inter-electrode delay interval may be set by the manufacturer of the IMD 100. Alternatively, the second inter-electrode delay may be obtained from the processes described with reference to FIGS. 3 and 4.

After setting the maximum AV delay, the maximum first inter-electrode delay and the maximum second inter-electrode delay, the flow moves to 510. At 510, the IMD 100 detects for sensed events, i.e., intrinsic events, in the right atrium and, if necessary, delivers pacing pulses to the atrium to maintain the atrium at a base rate. The base rate may be the rate at which the hearts chamber (atrium) beats. In one embodiment, the base rate may be 30-40 beats per minute (bpm). Alternatively, the base rate may be 60 bpm. For example, the base pacing rate may be calculated using an algorithm. Alternatively, the base rate may be pre-programmed in the IMD 100.

At 512, following a paced atrial event or a sensed atrial event, the flow pauses for the AV delay. At the end of the AV delay at 514, the process determines whether an intrinsic ventricular event is sensed at electrode E1, before the AV delay timed out. When an intrinsic ventricular event is sensed at electrode E1 before the end of the AV delay, the flow moves to 515 where the AV delay is decremented before flow returns to 510. The operations of blocks 510-515 are repeated until no intrinsic ventricular event is sensed at electrode E1 before the AV delay times out. Returning to 514, when no intrinsic ventricular event is sensed before the AV delay times out, the flow moves to junction 520 (FIG. 5B).

Figure 5B:
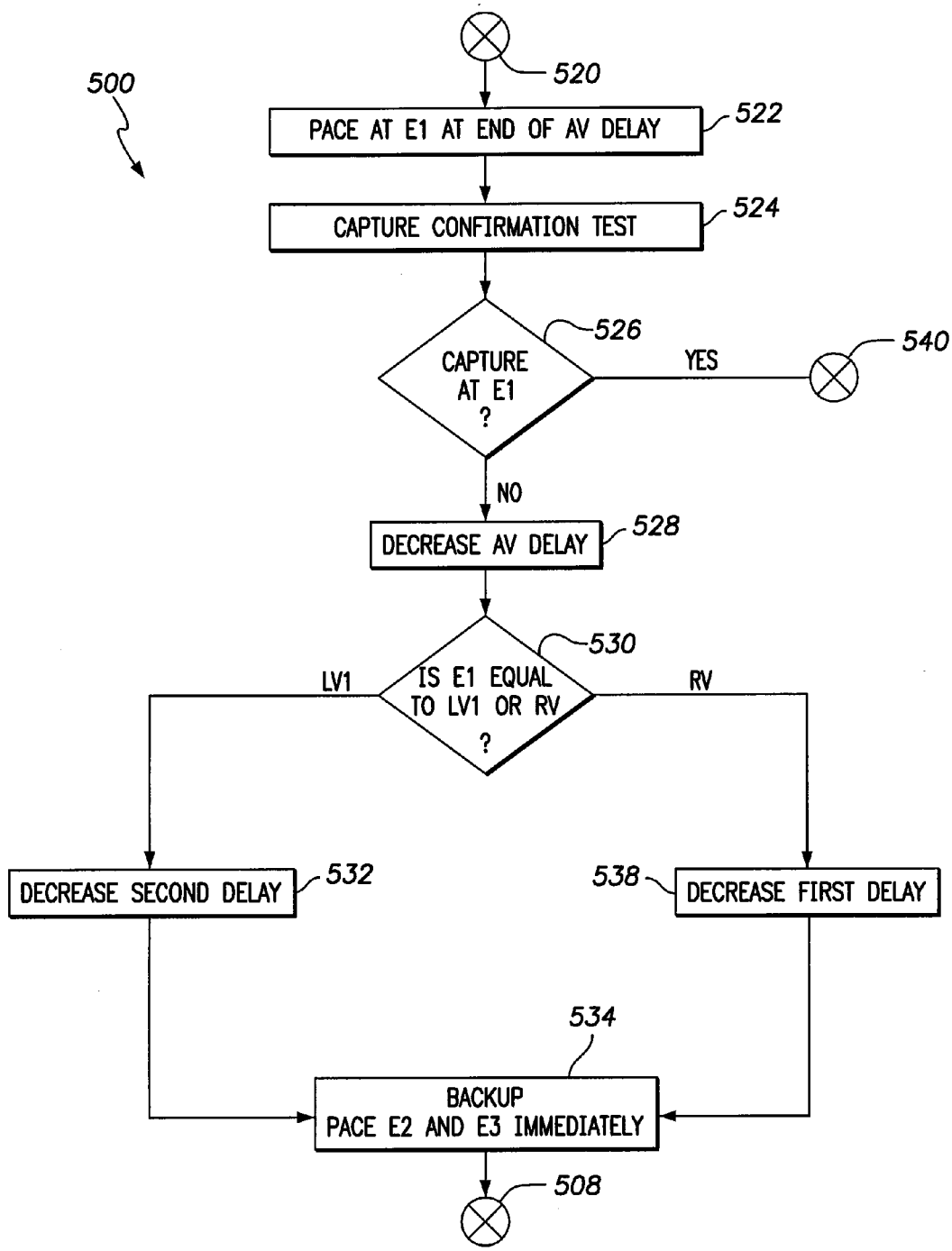

FIG. 5B illustrates the second part of the process 500. At 522, upon expiration of the AV delay the IMD 100 provides a pacing pulse at the first electrode E1. A capture confirmation test is performed, and the flow moves along 524. At 526, the process 500 checks for capture at the first electrode E1 before the paced event at the first electrode E1. A failure to capture at the first electrode E1 would arise when the timing of the pacing pulse at electrode E1 substantially coincides with the presence of intrinsic conduction at the site of electrode E1, thereby resulting in fusion. When there is no capture at the first electrode E1, before the paced event at the first electrode E1, the flow moves to 528 and a new AV delay value is set in an attempt to avoid fusion during subsequent cycles. The new AV delay is less than the prior AV delay value.

At 530, the process 500 determines whether the first electrode E1 corresponds to the first LV pacing site or the RV pacing site. When the first electrode E1 corresponds to the first LV pacing site, the second inter-electrode delay (the LV2RV delay) is decreased and forms the new second inter-electrode delay at 532. The decrease in the second inter-electrode delay compensates for any preceding decrease in the AV delay, and is intended to ensure that pacing pulses subsequently delivered at the third electrode E3 associated with the RV pacing site result in capture at that site as opposed to no capture at that site due to possible fusion with earlier-arriving intrinsic conduction resulting from the reduced AV delay.

If the first electrode E1 corresponds to the RV pacing site, the first inter-electrode delay (RVLV1 delay) is decreased, and forms the new first inter-electrode delay at 538. The decrease in the first inter-electrode delay compensates for any preceding decrease in the AV delay, and is intended to ensure that pacing pulses subsequently delivered at the second electrode E2 associated with the LV1 pacing site result in capture at that site as opposed to no capture at that site due to possible fusion with earlier-arriving intrinsic conduction resulting from the reduced AV delay.

At 534, the IMD 100 provides a pacing pulse at the second electrode E2 and a pacing pulse at the third electrode E3. These pacing pulses are provided as backup pacing pulses immediately after each inter-electrode delay adjustment without regard to any timing delays. The flow then moves to junction 508 and the process 500 is repeated. Returning to 526, when capture is detected at the first electrode E1, the flow moves to 540 (FIG. 5C).

Figure 5C:
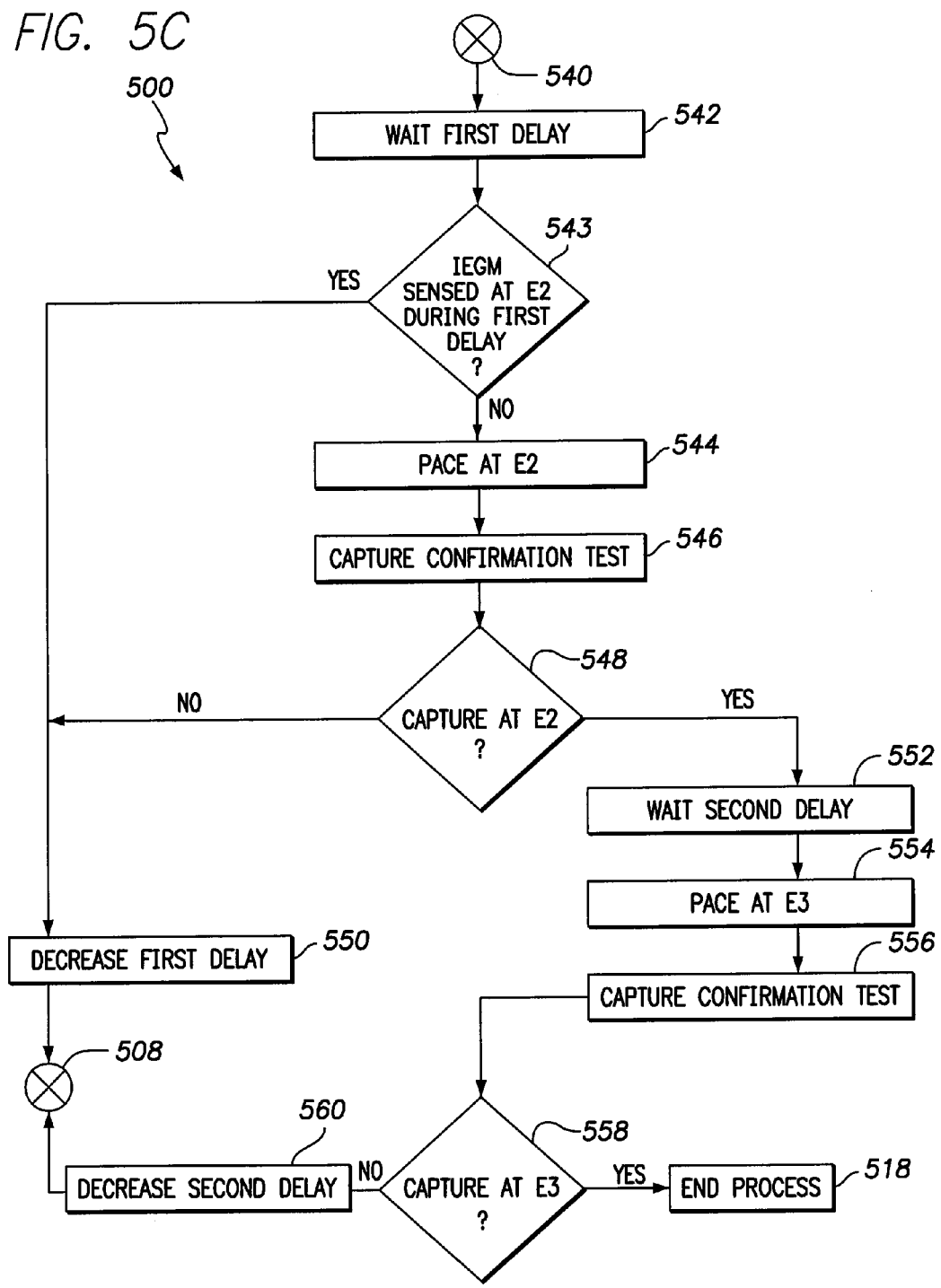

FIG. 5C illustrates the third part of the process 500. At block 542, the process 500 pauses for the first inter-electrode delay. During the first inter-electrode delay, at block 543 the IMD determines whether IEGM activity (due to intrinsic conduction) is sensed at the second electrode E2. If IEGM activity is sensed during this period, at block 550 the process 500 decreases the first inter-electrode delay value. After the first inter-electrode delay is decreased, the flow moves back to the junction 508 (FIG. 5A) and the process 500 is repeated. If IEGM activity is not sense then following the pause for the first inter-electrode delay, at block 544 the IMD 100 provides a pacing pulse at the second electrode E2. At 546, the process 500 performs another capture confirmation test. At 548, the process 500 determines whether there was capture at the second electrode E2. When there is capture, at block 550 the process 500 decreases the first inter-electrode delay value. After the first inter-electrode delay is decreased, the flow moves back to the junction 508 (FIG. 5A) and the process 500 is repeated.

Returning to 548, when capture occurs, flow moves to 552 where the process 500 pauses for the second inter-electrode delay. Following the pause for the second inter-electrode delay, at 554 the IMD 100 provides a pacing pulse at the third electrode E3. At 556, another capture confirmation test is performed. At 558, the process 500 checks whether capture confirmation occurs at the third electrode E3. When capture is not confirmed at the third electrode E3, the process 500 moves to 560 where the second inter-electrode delay is decreased; after which the flow moves back to the junction 508 (FIG. 5A) and the process 500 is repeated. Returning to 558, when capture is confirmed at the third electrode E3, the flow moves to 518 and the process ends.

As depicted in the processes 300, 400, and 500, the search for the respective inter-electrode delay is performed in a top down manner. The search starts out with the maximum allowable inter-electrode delay and recursively decreases the maximum inter-electrode delay so as to reach an inter-electrode delay value. In an alternate embodiment of the processes 300, 400, 500, searches for inter-electrode delays may be performed in a bottom to top manner. The bottom to top search may start out with the least allowable inter-electrode delay and recursively increase the inter-electrode delay until the inter-electrode delay is found that meets a criterion and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for determining pacing related timing of an IMD, said method comprising:

pacing at an RV pacing site, a first LV pacing site and a second LV pacing site in accordance with a first site, a second site and a third site pacing order, and further in accordance with a first inter-electrode pacing delay between pacing at the first site and pacing at the second site and a second inter-electrode pacing delay between pacing at the second site and pacing at the third site;

detecting for at least one of a sensed event or a paced event at each of the second site and the third site; and adjusting the first inter-electrode pacing delay and the second inter-electrode pacing delay to avoid sensed events in favor of paced events at each of the second site and the third site.

2. The method of claim 1 wherein adjusting comprises one or more of:

decreasing the first inter-electrode delay when a paced event is not detected at the second site; and decreasing the second inter-electrode delay when a paced event is not detected at the third site.

3. The method of claim 2 wherein the first site is the RV pacing site, the second site is the first LV pacing site, and the third site is the second LV pacing site.

4. The method of claim 1 wherein the pacing order of the first site, the second site and the third site is sequential.

5. The method of claim 1 further comprising:

subsequent to pacing the first site, detecting for a sensed event at each of the second site and the third site; and determining which, if any, of the second site and the third site is the first to experience a sensed event;

wherein if a sensed event is detected at the second site first, then adjusting comprises setting the first inter-electrode delay so that a paced event is detected at the second site prior to a sensed event being detected at the second site, and if a sensed event is detected at the third site first, then adjusting comprises setting the first inter-electrode delay so that a paced event is detected at the second site prior to a sensed event being detected at the third site.

6. The method of claim 1 further comprising:

subsequent to pacing the second site, detecting for a sensed event at each of the first site and the third site; and wherein if a sensed event is detected at the first site, then adjusting comprises decreasing the first inter-electrode delay, and if a sensed event is detected at the third site, then adjusting comprises setting the second inter-electrode delay so that a paced event is detected at the third site prior to a sensed event being detected at the third site.

7. The method of claim 1 further comprising:

subsequent to pacing at the third site, detecting for a sensed event at the first site and the second site; and wherein if a sensed event is detected at either of the first site or the second site, then adjusting comprises decreasing the second inter-electrode delay.

8. The method of claim 1 further comprising adjusting an atrioventricular delay in response to detection of either of a sensed event at the first site or a failure to detect a paced event at the first site.

9. The method of claim 8 further comprising if a paced event is not detected at the first site, decreasing one of the first inter-electrode delay and the second inter-electrode delay.

10. The method of claim 9 wherein if the first site is the RV pacing site then the first-inter-electrode delay is decreased.

11. The method of claim 8 further comprising:

if a paced event is detected at the first site, detecting for one of a sensed event at the second site during the first inter-electrode delay or a paced event at the second site; and wherein adjusting comprises decreasing the first inter-electrode delay in response to detection of either a sensed event at the second site or failure to detect a paced event at the second site.

12. The method of claim 11 further comprising:

if a paced event is detected at the second site, then pacing comprises pacing at the third site and detecting comprises detecting for a paced event at the third site; and wherein if a paced event is not detected at the third site, then adjusting comprising decreasing the second inter-electrode delay.

13. An implantable medical device (IMD), comprising:

a plurality of electrodes configured to be associated with an RV pacing site, a first LV pacing site and a second LV pacing;

a pulse generator configured to deliver pacing pulses to the plurality electrodes in accordance with a first site, a second site and a third site pacing order, and further in accordance with a first inter-electrode pacing delay between pacing at the first site and pacing at the second site and a second inter-electrode pacing delay between pacing at the second site and pacing at the third site;

a processor configured to detect at least one of a sensed event or a paced event at each of the second site and the third site; and a pacing parameter control module (PCM) configured to adjust the first inter-electrode pacing delay and the second inter-electrode pacing delay to avoid sensed events in favor of paced events at each of the second site and the third site.

14. The system of claim 13 wherein the PCM is configured to:

decrease the first inter-electrode delay when a paced event is not detected at the second site; and decrease the second inter-electrode delay when a paced event is not detected at the third site.

15. The system of claim 14 wherein the first site is the RV pacing site, the second site is the first LV pacing site, and the third site is the second LV pacing site.

16. The system of claim 13 wherein the pacing order of the first site, the second site and the third site is sequential.

* * * * *